United States Patent
Welander et al.

[11] Patent Number: 4,534,048
[45] Date of Patent: Aug. 6, 1985

[54] METHODS OF INCREASING ANTERIOR LAYER THICKNESS OF CONTINUOUS DENTAL IMAGES OBTAINED THROUGH ROTATIONAL PANORAMIC RADIOGRAPHY

[75] Inventors: Ulf E. S. Welander, Umea, Sweden; William D. McDavid; Charles R. Morris, both of San Antonio, Tex.

[73] Assignee: Pennwalt Corporation, Philadelphia, Pa.

[21] Appl. No.: 455,095

[22] Filed: Jan. 3, 1983

[51] Int. Cl.³ .................. G01N 21/00; G01N 23/00; G03B 41/16
[52] U.S. Cl. .......................................... 378/39; 378/38
[58] Field of Search .................... 378/38, 39, 40

[56] References Cited
U.S. PATENT DOCUMENTS 4,251,730 2/1981 Cushman ........................ 378/40
4,321,472 3/1982 Cushman ........................ 378/38
4,340,971 1/1982 Furuichi ........................ 378/40

Primary Examiner—Alfred E. Smith
Assistant Examiner—Charles F. Wieland
Attorney, Agent, or Firm—Seidel, Gonda, & Goldhammer

[57] ABSTRACT

Effective centers of rotation of the X-ray beams when projecting the anterior regions are caused to be disposed considerably more interiorly of the dental arch, i.e., farther from the incisors and closer to the X-ray source, to thus provide longer projection radii of the beams at the anterior region. Lengthening of the projection radii is achieved through unique velocity profiles of patient chair movement along an x-axis and film travel within the camera. The longer effective projection radii of beams at the anterior region provide for a substantially wider or thicker layer thereat with a concomitant modest narrowing of the layer at the canine regions.

11 Claims, 6 Drawing Figures

METHODS OF INCREASING ANTERIOR LAYER THICKNESS OF CONTINUOUS DENTAL IMAGES OBTAINED THROUGH ROTATIONAL PANORAMIC RADIOGRAPHY

STATEMENT OF THE INVENTION

The present invention relates to dental radiography and more particularly concerns methods for improving rotational panoramic radiographic techniques to obtain image portrayals having increased layer thickness at the anterior regions.

BACKGROUND AND SUMMARY OF THE INVENTION

A serious disadvantage of current dental X-ray machines employing rotational panoramic radiographic techniques for producing continuous image radiographs is that the resultant has a very narrow layer in the anterior region. Not only are the images excessively narrow at the anterior region, but the images thereat are often distorted and unsharp due to improper patient positioning while the anterior region is being radiographed.

The thin image layer at the anteriors produced by many current panoramic dental X-ray machines results from a very small effective projection radius at the anterior region during rotational scan thereof by the X-ray beams. If the projection radius at the anterior region could be increased without a concomitant distortion or inaccurate portrayal of the remaining dental arch and temporomandibular joint area, the layer at the anterior region could be widened and patient positioning would therefore not be so extremely critical.

We have discovered that the effective projection radius at the anterior region may be lengthened if the effective center of rotation of the X-ray beams are caused to retreat immediately after a canine is projected until completion of the radiographing of one-half the incisors, and the path of the effective centers of rotation of the X-ray beams then proceeds to trace a mirror image of the retreat path until the entire anterior region is radiographed. The retreat, or reversal, or backward movement of the effective centers of rotation of the beams within the dental arch toward the X-ray source may be achieved by controlling the movement of the patient chair and adjusting film travel speed accordingly, both later described.

As is known, rotational panoramic radiography may include employment of mechanisms for controlling film travel speed; orbiting the X-ray tubehead and camera assembly about the head of the patient; and shifting the patient chair in accordance with predetermined patterns. Each of these movements must be painstakingly integrated and synchronized if meaningful continuous radiographs are to be provided. Structure for providing such continuous image radiographs employing rotational panoramic radiographic techniques are shown and described in U.S. Pat. No. 4,251,730, assigned to the present assignee hereof. The subject matter of U.S. Pat. No. 4,251,730 is herein incorporated by reference and relates to an x-motion drive for moving or transporting the patient chair in a straight line, as the patient chair moves in the present invention, as opposed to x-y or non-straight line chair movement.

Briefly, the panoramic dental X-ray machine described in U.S. Pat. No. 4,251,730 may be slightly modified by any of a number of suitable means to provide the improved layer thickness at the anterior region. For example, in order to achieve the aforediscussed desired backward movement of the effective centers of rotation of the X-ray beams in accordance with one aspect of the present invention, the patient chair movement was altered by configuring the path of groove 256 in cam member 244 (U.S. Pat. No. 4,251,730) in accordance with readily calculable mathematical values. Grooving a different path for each cam for each new chair movement however is costly and time-consuming.

The desired chair movements may otherwise be achieved by suitable x-motion drives; y-motion drives; x-y motion drives; a stationary patient chair with an X-ray tubehead following a predetermined path; or combinations thereof. Preferably, however, a more versatile chair movement control includes a stepper motor controlled by microprocessor means wherein signals or impulses generated thereby are fed to the motor for transmitting desired motion to the chair.

Film travel speed is made proportional to the effective projection radius, i.e., the longer the effective projection radius, the faster the film should travel in the camera. Film drive mechanisms and structure associated therewith are shown and described in the following U.S. Pat. Nos., all assigned to the present assignee: 4,172,977; 4,194,121; 4,221,970; 4,247,779; 4,287,423; and 4,304,998.

Film travel speed is similarly preferably controlled by microprocessor means connected to a suitable stepper motor. Programming of microprocessors is well known for performing specified functions and is not herein shown or described.

The present invention is directed to and discloses methods for increasing the effective projection radius at the incisors or anterior region by providing a backward or reverse movement to the effective centers of rotation of the X-ray beams by means of controlling chair movement and film speed. Any of the suitable means abovementioned for providing the desired velocity profiles to the chair movement and film speed may be used. By thus increasing the effective projection radii at the anterior region, an improved wider layer thereat results.

DETAILED DESCRIPTION OF THE INVENTION

In a typical panoramic dental X-ray machine manufactured and sold by the assignee of the present invention for providing continuous radiographic images of the dental arch and temporomandibular joint areas, hereinafter referred to as the TMJ areas, the patient is seated in a patient chair and positioned with respect to the tubehead-camera assembly. The tubehead-camera assembly circularly orbits the patient, situated in the beam path, on an imaginary axis, pivot point, or center of rotation. That is, X-ray beams are generated and projected from the X-ray tube contained within the tubehead from an imaginary pivot point or center of rotation when radiographing the dental arch and TMJ areas. Because the patient chair however is caused to move, along an x-axis in the present invention, the centers of rotation of the beams shift along the x-axis with respect to the patient seated in the moving chair. The effective or functional centers of rotation however travel a different path, later described.

Figure 1:
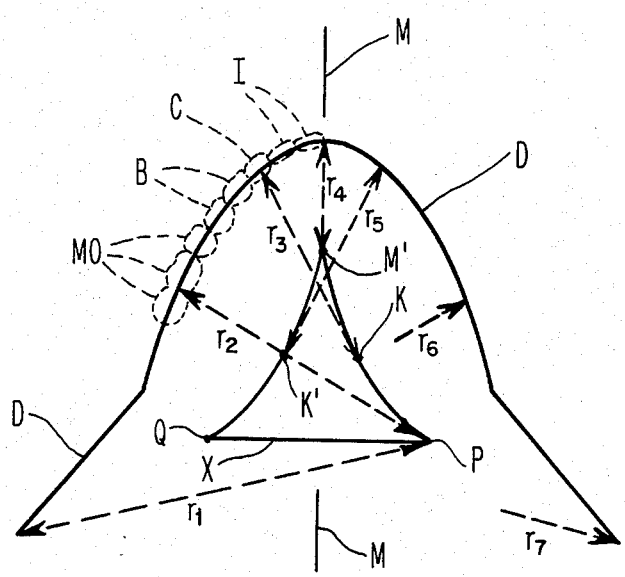
FIG. 1 diagrammatically illustrates a typical movement pattern employed in prior art rotational panoramic radiography of the effective centers of rotation of representative X-ray beams.

Reference is now made to FIG. 1 of the drawings which illustrates a typical movement pattern of the effective centers of rotation of representative X-ray beams generated by the X-ray tube contained within the circularly orbiting tubehead of a typical panoramic dental X-ray machine of the assignee of the present invention. A typical dental arch D with TMJ areas is shown with median line M. Line X defines the path of movement of the patient chair along an x-axis.

In radiographing the left half of the dental arch D and TMJ area, a representative X-ray beam $r_1$ is projected to a posterior portion of the jaws, as shown. As the tubehead-camera assembly continues to orbit the patient, another representative beam $r_2$ is projected to the molar area MO several seconds subsequent to the generation of beam $r_1$. Beams $r_1$ and $r_2$, and others thereinbetween, are generated from imaginary point P. The beams thus generated have a relatively long effective projection radius as indicated by the length of the dotted lines, which effective projection radii decrease in length successively during further rotational movement of the X-ray tubehead until beam $r_4$ is projected at the center of the incisors I or anterior region, coincident with median line M.

The projection radii of the X-ray beams projected between beams $r_3$ at the canine tooth C and $r_4$ are successively shortened in length due to movement of the chair to the left along line X. Since dental arches are not circular, or elliptical, but represent a complex curve, the chair must be moved in accordance with predetermined movements as well as the speed of travel of the X-ray film within the orbiting camera if proper spacing and distances occupied by each tooth along the dental arch is to be portrayed without distortion and unsharpness. Movement of the chair however causes the effective centers of rotation of the X-ray beams to follow a curved path, i.e., along line PKM' while the left half of the dental arch and TMJ area are being radiographed.

To further clarify, representative beam $r_3$ has an effective center of rotation at point K on line PKM' while the pivot point or imaginary center of rotation of the beam lies somewhere on line X, but closer to point P. Beam $r_3$ is tangential to line PKM' at point K. Each of the beams projected between beams $r_2$ and $r_4$, including bicuspids B, are tangential to line PKM' the points of tangency ascending from point P to point M' as the tubehead continues its constant speed, uninterrupted circular orbiting of the patient.

Beam $r_4$ has an effective center of rotation at point M', its pivot point or imaginary center of rotation lying midway between points P and Q on line X.

After beam $r_4$ has been generated, representative beam $r_5$ is projected. Beam $r_5$ traces a mirror image of beam $r_3$, having an effective center of rotation at point K' on line QK'M'. Similarly, beams $r_6$ and $r_7$ trace mirror images of beams $r_2$ and $r_1$ respectively, having their effective and imaginary center of rotation at point Q.

The effective projection radius of any beam may be defined as the distance between the effective center of rotation of that beam and the center of the layer, or tooth being radiographed. This distance suffers its minimum value in the anterior region. Since layer thickness has been discovered to be dependent upon the effective projection radius, the layer thickness is narrowest in the anterior region.

Figure 2:
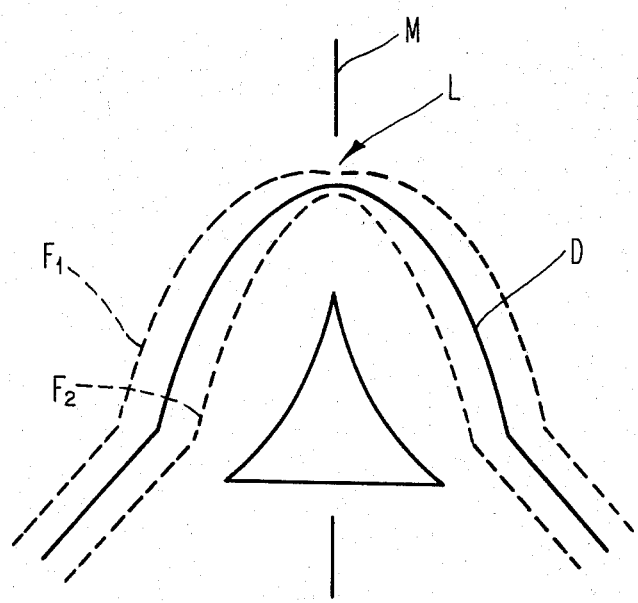
FIG. 2 illustrates the dental arch and temporomadibular joint area thickness from the typical prior art movement pattern shown in FIG. 1.

Typical radiographic images produced as a result of the abovedescribed combined movements of the chair, film, and orbiting X-ray beams exhibited a very narrow layer L at the anterior region (FIG. 2). The layer (referred to as the "focal trough" in U.S. Pat. No. 4,251,730) where images are sharp for the dental arch and TMJ area is illustrated as bound by two dashed lines, one line $F_1$ drawn exteriorly the line D representing the dental arch and another line $F_2$ drawn interiorly thereof. Using a criterion of 0.5 mm relative motion unsharpness, i.e., the image is unclear beyond 0.5 mm exteriorly line $F_1$ and interiorly line $F_2$, the layer L at the anterior region has a narrow width of only 4.5 mm as compared to a layer width of 10 mm at the anterior region when the methods of the present invention are practiced, later discussed.

In obtaining data for FIGS. 1 and 2, the patient's chair remains substantially motionless for about the initial and final $6\frac{1}{2}$ seconds of film travel and tubehead-camera assembly rotation. Referring to FIGS. 8 and 16 of U.S. Pat. No. 4,251,730, the tubehead-camera assembly therein described, and in the present invention, requires about 22 seconds to complete its rotation of approximately 240°.

Figure 3:
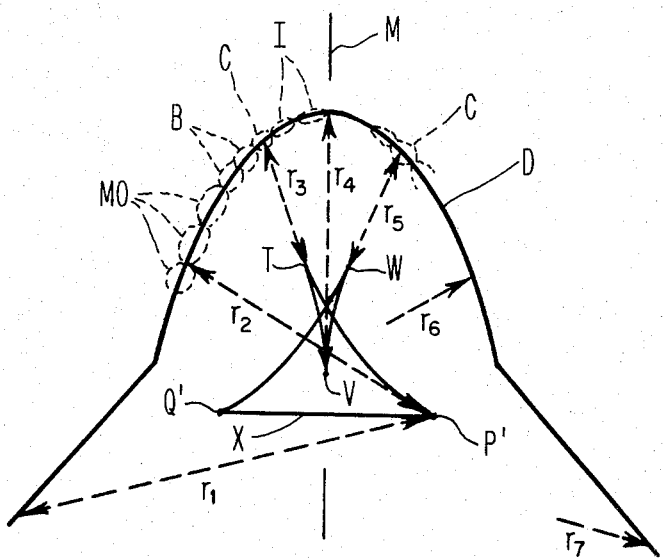
FIG. 3 diagrammatically illustrates an improved movement pattern in rotational panoramic radiography of the effective centers of rotation of representative X-ray beams in accordance with the present invention.
Figure 4:
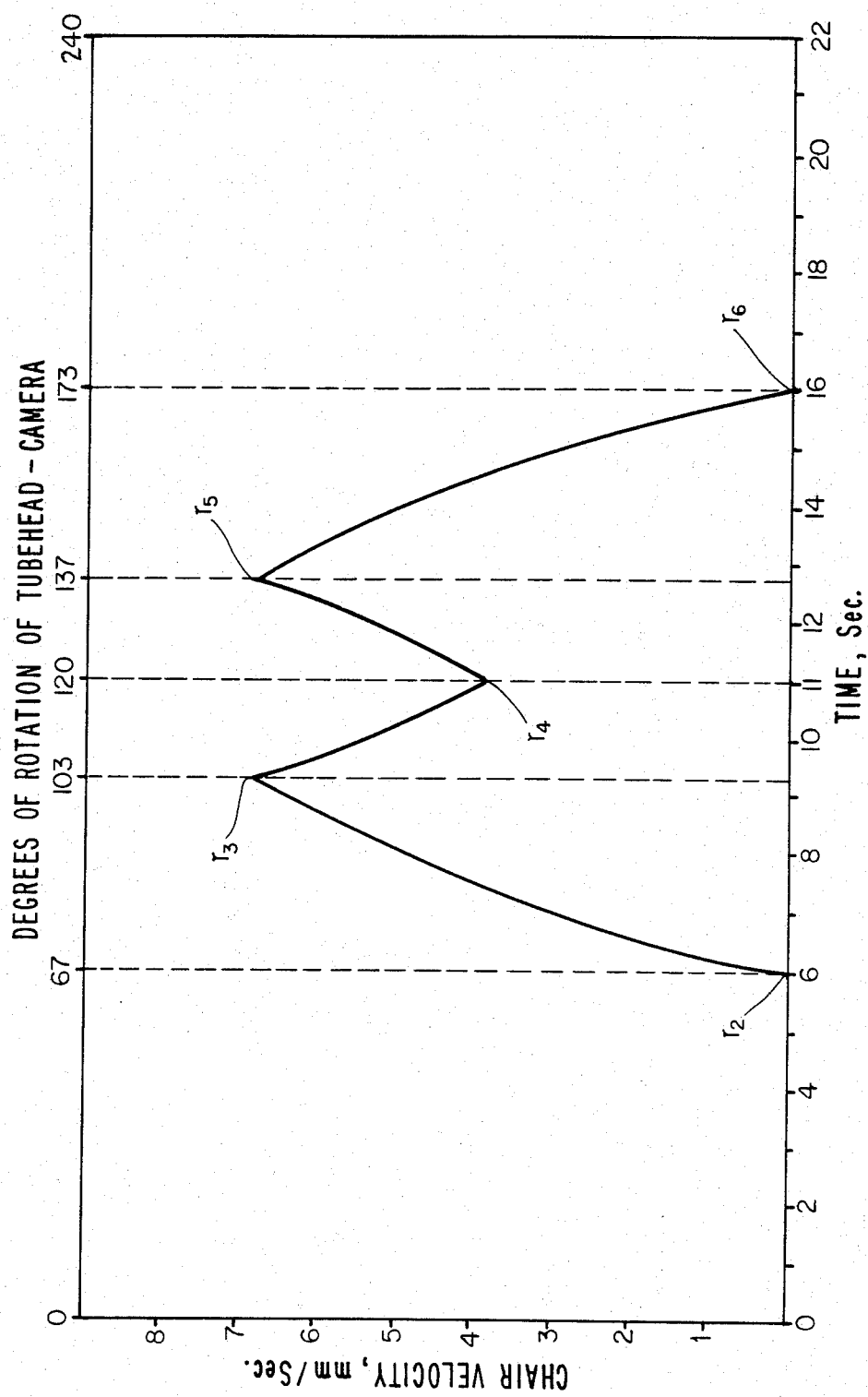
FIG. 4 is a graphic representation of patient chair velocity plotted against degrees of rotation of tubehead-camera assembly and time consumed therefor.
Figure 5:
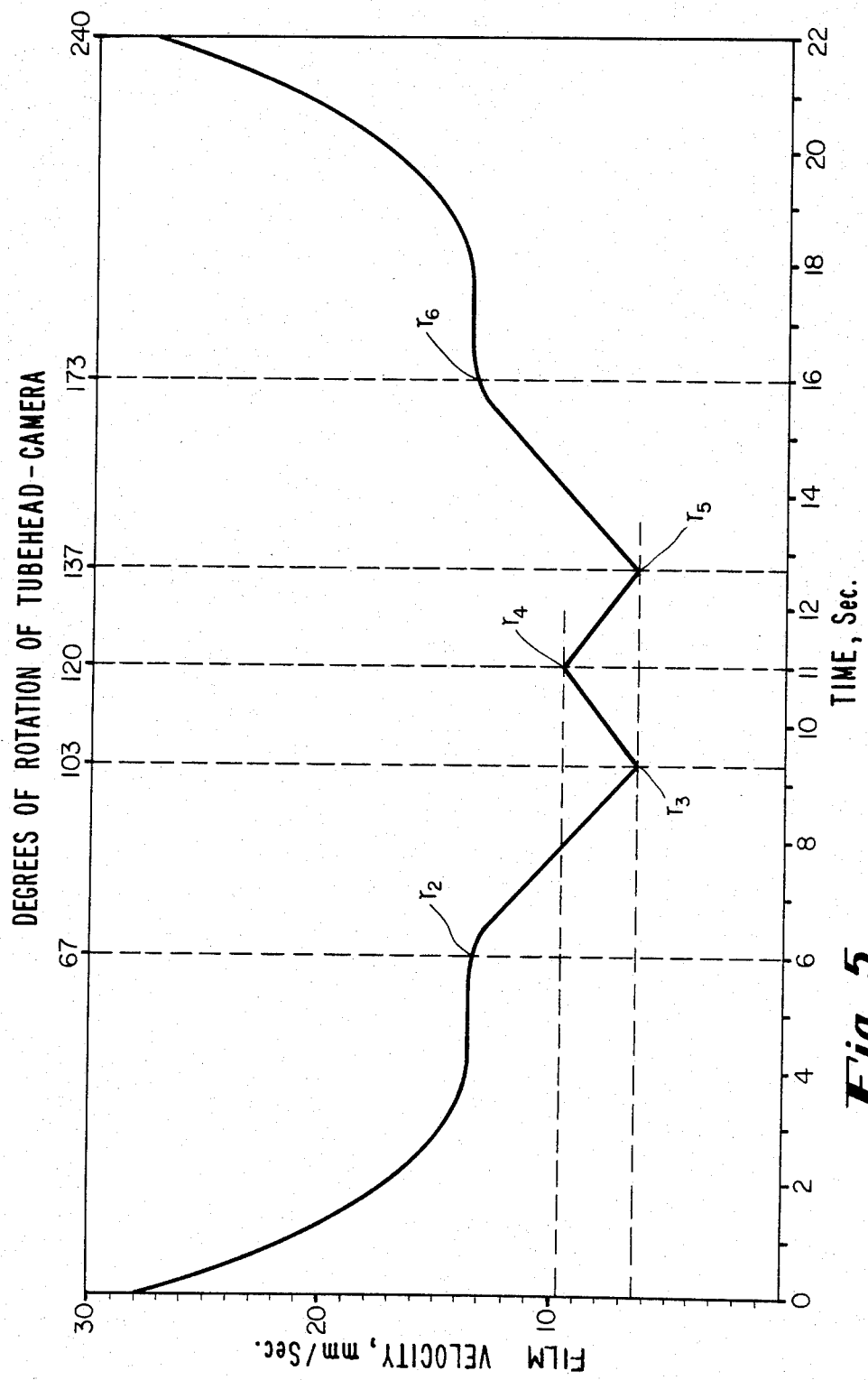
FIG. 5 is a graphic representation of film travel speed plotted against degrees of rotation of tubehead-camera assembly and time consumed for such rotation.

Referring now to FIGS. 3, 4 and 5 of the drawings of the present invention, beams $r_1$ and $r_2$ have a center of rotation at point P'. Immediately after beam $r_2$ is projected at the molar region MO, i.e., about 6 seconds or 67° of tubehead rotation, the patient chair starts to move, accelerating along the x-axis substantially uniformly for about $3\frac{1}{3}$ seconds or about 36° of tubehead rotation until a maximum velocity of almost 7 mm/second is attained. Simultaneously therewith (FIG. 5), film travel speed is decreased accordingly from about 14 mm/second to about $6\frac{1}{2}$ mm/second.

The patient chair then immediately decelerates substantially uniformly for the next $2\frac{2}{3}$ seconds, or about 17° of tubehead rotation, until the median point, represented by line M, or after about 11 seconds or 120° of tubehead rotation, at which time the chair is traveling approximately 4 mm/second, while the film speed or velocity is increasing generally linearly to about $9\frac{1}{2}$ mm/second, after which, both chair and film immediately trace a mirror image of their respective velocity profiles until completion of radiographing.

Referring again to FIG. 3 beam $r_3$ is projected at canine tooth C after about $9\frac{1}{3}$ seconds of operation, or about 103° of tubehead rotation. The effective center of rotation of beam $r_3$ is located at point T. Beams projected between beams $r_2$ and $r_3$ have effective centers of rotation between points P' and T on curved line P'T and tangential thereto.

As abovementioned, the chair decelerates for about $2\frac{2}{3}$ seconds immediately prior to projection of beam $r_4$ causing the effective centers of rotation to retreat along line VT. Thus, beams projected between beams $r_3$ and $r_4$ have effective centers of rotation along line VT and tangential thereto. The effective center of rotation for beam $r_4$ is located at point V.

Beam $r_5$ has an effective center of rotation at point W and traces a mirror image of beam $r_3$ as the tubehead continues to orbit beyond line M. Beams projected between beams $r_4$ and $r_5$ have effective or functional centers of rotation along curve WV and tangential thereto, in a manner identical to beams projected between beams $r_3$ and $r_4$ having effective centers of rotation along line VT. Beams $r_6$ and $r_7$ have centers of rotation at point Q'. Beams projected between beams $r_5$ and $r_6$ have effective centers of rotation along line Q'W and tangential thereto.

Velocities or speeds of chair movement and film travel when beams $r_2$ through $r_6$ are projected are indicated in FIGS. 4 and 5 as well as the inverse relationship existing between the two coordinated speeds.

Figure 6:
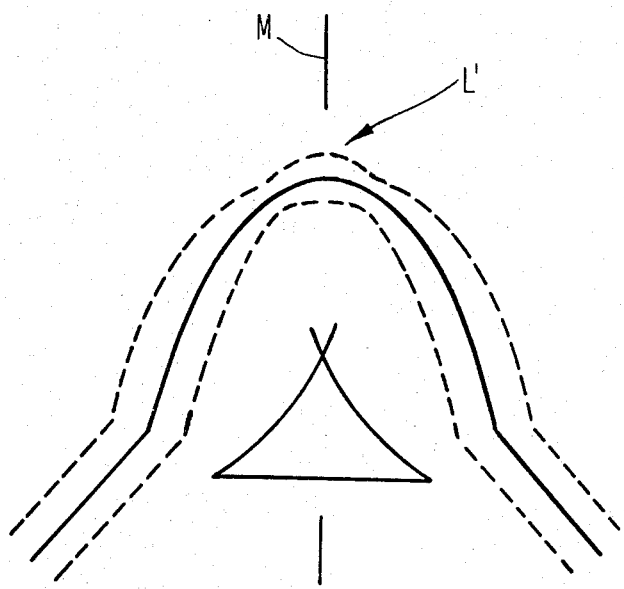
FIG. 6 illustrates improved layer thickness of the dental arch and temporomandibular joint area resulting from the movement pattern depicted in FIG. 3.

When the anterior regions of FIGS. 1 and 3 are compared, it is apparent that the effective projection radius of beam $r_4$ of FIG. 3 is considerably longer than its counterpart beam in FIG. 1. Since, as aforementioned, layer thickness is dependent upon effective projection radius, the layer thickness L' of FIG. 6, reflecting the movement pattern illustrated in FIG. 3, is substantially wider than the layer thickness L of FIG. 2. The width of layer L' is approximately 10 mm, an increase of over 100% over the width of layer L of FIG. 2.

The widening of the layer at the anterior region is achieved at the expense of the canine region where its layer is narrowed, but by an amount less than 20%. As illustrated in FIG. 3, beams $r_3$ and $r_5$, projected in the general direction of the canines, have the smallest effective projection radii of the entire dental arch and TMJ area. The gain in the anterior region I however is considerably greated than the loss suffered in the canine regions C.

We claim:

1. In a rotational panoramic radiographic method for widening the layer of a dental arch at an anterior region thereof of a patient seated in a moving chair orbited by a tubehead-camera assembly to produce moving effective centers of rotation of X-ray beams projected from said tubehead, and means to move film within said camera at a non-linear speed, the improvement comprising the step of causing said effective centers of rotation of beams projecting said anterior region to be displaced more interiorly of said dental arch than effective centers of rotation of beams projecting canine regions.

2. In a method for widening the layer at the anterior region of dental images obtained through rotational panoramic radiographic techniques wherein a patient chair is mounted for movement along an x-axis and a tubehead-camera assembly orbits the patient chair, and wherein said tubehead contains an X-ray source for generating X-ray beams and said camera contains film to be activated by said beams after passing through a dental arch of a patient seated in said chair, and wherein beams from said orbiting tubehead have effective centers of rotation in accordance with a position of said chair along said x-axis, and wherein means are provided for moving said film in said camera at non-linear speeds and for powering said X-ray source, the improvement for widening said layer comprising the step increasing an anterior region projection radii length of said beams, said anterior region protection radii length being greater than a canine region projection radii length of said beams by
 causing said effective centers of rotation of beams projecting said anterior region to be displaced inwardly within said arch from said canine regions.

3. In a method for widening the layer at the anterior region of dental images obtained through rotational panoramic radiographic techniques wherein a patient chair is mounted for movement along an x-axis and a tubehead-camera assembly orbits the patient chair, and wherein said tubehead contains an X-ray source for generating X-ray beams and said camera contains film to be activated by said beams after passing through a dental arch, said dental arch including a temporomandibular joint area of a patient seated in said chair, and wherein beams from said orbiting tubehead have effective centers of rotation in accordance with a position of said chair along said x-axis, and wherein means are provided for moving said film in said camera at non-linear speeds and for powering said X-ray source, the improvement for widening said layer comprising the step of creating a plurality of said effective centers of rotation of beams projecting images of said arch, said effective centers of rotation of beams projecting said anterior region being displaced further interiorly within said arch than effective centers of rotation at canine regions of said arch.

4. Method of claim 3 wherein said effective centers of rotation of beams at said anterior region provide longer effective projection radii than corresponding effective projection radii formed at said canine regions.

5. Method of claim 3 wherein positions of said effective centers of rotation of beams at said anterior region are effected by movement comprising the steps of decelerating the speed of travel of said chair substantially uniformly from one of said canine regions to a midpoint of incisors of said arch,
 immediately accelerating speed of travel of said chair substantially uniformly to other of said canine regions, said chair travel speed being substantially identical at each of said canine regions, and
 controlling speed of travel of said film to vary inversely with speed of travel of said chair.

6. In a method for widening the layer at the anterior region of dental images obtained through rotational panoramic radiographic techniques wherein a patient chair is mounted for movement along an x-axis and a tubehead-camera assembly orbits the patient chair, and wherein said tubehead contains an X-ray source for generating X-ray beams and said camera contains film to be activated by said beams after passing thorough a dental arch of a patient seated in said chair, and wherein beams from said orbiting tubehead have effective centers of rotation in accordance with a position of said chair along said x-axis, and wherein means are provided for moving said film in said camera at non-linear speeds and for powering said X-ray source, the improvement for widening said layer comprising the step of substantially uniformly accelerating said chair speed while radiographing molar region to canine region on one side of said arch to create a plurality of moving effective centers of rotation of orbiting beams, said effective centers of rotation of said beams at said canine region providing effective projection radii of specific lengths, immediately substantially uniformly decelerating said chair speed until a mid-point of incisors are radiographed to create a plurality of additional effective centers of rotation of orbiting beams providing effective projection radii of greater length than said projection radii of said specific lengths, continuing radiographing the remainder of said incisors and said dental arch to create mirror images of said effective centers of rotation and projection radii at the other side of said dental arch, and controlling said speed of said film within said camera to vary inversely with speed of travel of said chair.

7. Method of claim 6 further characterized by the step of maintaining said chair stationary until said chair speed is substantially uniformly accelerated when radiographing said molar region to said canine region.

8. Method of claim 7 wherein rotation of said tubehead-camera assembly requires about 240° and consumes about 22 seconds for radiographing dental arch and temporomandibular joint areas of said patient, and widening of said layer comprises additional steps of substantially uniformly accelerating chair velocity from an initial stationary position maintained thereat for about 6 seconds of tubehead rotation to its maximum speed of almost 7 mm/second in a period slightly in excess of 3 seconds, immediately substantially uniformly decelerating chair velocity to slightly less than 4 mm/second within a period of slightly less than 2 seconds to complete radiographing of one-half said dental arch and temporomandibular joint area, continuing radiographing remaining one-half of said dental arch and temporomandibular joint area in substantially reverse speed and time from initial one-half, and controlling speed of travel of said film to vary inversely with speed of travel of said chair.

9. Method of claim 8 further characterized by steps of controlling speed of travel of said film to about $6\frac{1}{2}$ and $9\frac{1}{2}$ mm/second respectively when said chair is traveling at said maximum speed of almost 7 mm/second and slightly less than 4 mm/second after said one-half of the dental arch and temporomandibular joint area are radiographed.

10. A method for widening the anterior region layer images of a dental arch obtained by rotational panoramic radiographic techniques comprising the steps of:
  (a) initiating rotation at a constant angular speed of a tubehead-camera assembly about a patient chair,
  (b) initiating a film movement at a film speed of about 14 mm/second within said tubehead-camera assembly simultaneously with the initiation of rotation of tubehead-camera assembly,
  (c) maintaining the patient chair motionless for about an initial 6 seconds of the tubehead-camera assembly rotation,
  (d) substantially uniformly accelerating the patient chair along an x-axis for about $3\frac{1}{2}$ seconds to a maximum chair velocity of about 7 mm/second after maintaining the patient chair motionless,
  (e) decelerating the film speed to about $6\frac{1}{2}$ mm/second simultaneously with the acceleration of the patient chair,
  (f) decelerating the patient chair for about $2\frac{2}{3}$ seconds to a velocity of about 4 mm/second until a mid-point of the dental arch is reached,
  (g) accelerating the film speed to about $9\frac{1}{2}$ mm/second simultaneously with the deceleration of the patient chair, and until a mid-point of the dental arch is reached, and
  (h) causing the movement of the tubehead-camera assembly and the film to retrace the initial movement of the tubehead-camera assembly and the film in a mirror image fashion.

11. A method for widening the anterior region layer images of a dental arch obtained by rotational panoramic radiographic techniques comprising the steps of:
  (a) initiating rotation at a constant angular speed of a tubehead-camera assembly about a patient chair, said tubehead-camera assembly being initially directed at a temporomandibular joint area of a jaw,
  (b) initiating a film movement at a film speed of 14 mm/second within said tubehead-camera assembly simultaneously with the initiation of rotation of tubehead-camera assembly,
  (c) maintaining the patient chair motionless until the tubehead-camera assembly rotation is directed to about a molar region of the jaw,
  (d) substantially uniformly accelerating to a maximum chair velocity of about 7 mm/second the patient chair along an x-axis after maintaining the patient chair motionless and until the tubehead-camera assembly is directed to a canine tooth of the jaw,
  (e) decelerating the film speed to about $6\frac{1}{2}$ mm/second, simultaneously with the acceleration of the patient chair,
  (f) decelerating the patient chair to a velocity of about 4 mm/second until a mid-point of an incisor region of the jaw is reached,
  (g) accelerating the film speed until the film speed is about $9\frac{1}{2}$ mm/second and a mid-point of the incisor region of the jaw is reached simultaneously with the deceleration of the patient chair, and
  (h) causing the movement of the tubehead-camera assembly and the film to retrace the initial movement of the tubehead-camera assembly and the film in a mirror image fashion.

* * * * *